US006544581B1

(12) United States Patent
Shrikhande et al.

(10) Patent No.: US 6,544,581 B1
(45) Date of Patent: Apr. 8, 2003

(54) PROCESS FOR EXTRACTION, PURIFICATION AND ENRICHMENT OF POLYPHENOLIC SUBSTANCES FROM WHOLE GRAPES, GRAPE SEEDS AND GRAPE POMACE

(75) Inventors: Anil J. Shrikhande, Madera, CA (US); Edward J. Race, Madera, CA (US); JoLynne D. Wightman, Fresno, CA (US); Robert D. Sambueso, Fresno, CA (US)

(73) Assignee: Canandaigua Wine Company, Inc., Madera, CA (US)

( * ) Notice: Subject to any disclaimer, the term of this patent is extended or adjusted under 35 U.S.C. 154(b) by 70 days.

(21) Appl. No.: 09/599,333

(22) Filed: Jun. 22, 2000

Related U.S. Application Data

(60) Provisional application No. 60/140,378, filed on Jun. 22, 1999.

(51) Int. Cl.⁷ .............................. A23L 1/28; A23L 1/29
(52) U.S. Cl. .................. 426/655; 426/590; 426/541; 426/425; 426/427; 424/195.1
(58) Field of Search ................ 426/655, 590, 426/541, 425, 427; 424/195.1

(56) References Cited

U.S. PATENT DOCUMENTS

| | | | |
|---|---|---|---|
| 3,436,407 A | 4/1969 | Masquelier | 514/456 |
| 4,698,360 A | 10/1987 | Masquelier | 514/456 |
| 5,484,594 A | 1/1996 | Frangi et al. | 424/195.1 |
| 5,773,262 A | * 6/1998 | Ariga et al. | 435/118 |
| 5,814,494 A | * 9/1998 | Ariga et al. | 435/118 |
| 5,912,363 A | 6/1999 | Nafisi-Movaghar et al. | 549/399 |
| 5,968,517 A | * 10/1999 | Duncan et al. | 424/195.1 |
| 6,165,475 A | * 12/2000 | Crea et al. | 424/195.1 |
| 6,210,681 B1 | * 4/2001 | Walker | 424/195.1 |
| 6,358,542 B2 | * 3/2002 | Cuomo et al. | 424/777 |
| 6,375,992 B1 | * 4/2002 | Blumenstein-Stahl et al. | 424/729 |

FOREIGN PATENT DOCUMENTS

| | | | |
|---|---|---|---|
| JP | 409221484 | * | 8/1997 |
| WO | WO 00/49115 | * | 8/2000 |

OTHER PUBLICATIONS

Demrow, H.S. et al., "Administration of Wine and Grape Juice Inhibits In Vivo Platelet Activity and Thrombosis in Stenosed Canine Coronary Arteries." Circulation, vol. 91, No. 4, pp. 1182–1188, 1995.

Frankel E. et al., "Inhibition of oxidation of human low–density lipoprotein by phenolic substances in red wine." Lancet vol. 34, pp. 454–457, 1993.

Frankel E. et al., "Commercial Grape Juices Inhibit the In Vitro Oxidation of Human Low–Density Lipoproteins." J. Agric. Food Chem., vol. 46, pp. 834–838, 1998.

Kantz, K. et al., "Isolation and Determination of Polymeric Polyphenols Using Sephadex LH–20 and Analysis of Grape Tissue Extracts." Am. J. Enol. Vitic., vol. 41, No. 3, pp. 223–228, 1990.

Prieur, C. et al., "Oligomeric and Polymeric Procyanidines From Grape Seeds." Phytochemistry, vol. 36, No. 3, pp. 781–784, 1994.

Renaud, S. et al., "Wine, alcohol, platelets and the French Paradox for coronary heart disease." Lancet vol. 339, pp.1523–1526, 1992.

* cited by examiner

*Primary Examiner*—Nina Bhat
(74) *Attorney, Agent, or Firm*—Kenyon & Kenyon (57) ABSTRACT

The present invention provides a novel process for extraction, purification and concentration of polyphenol substances from whole grapes, grape seeds and grape pomace without the need for membrane filtration. Aspects of several embodiments of the novel processes include hot water extraction, a dual pH treatment of the hot water extracts, and the uses of a copolymer of trimethylolpropane trimethacrylate as an adsorbent resin to maximize the concentration and purification of the beneficial polyphenolic substances.

70 Claims, 5 Drawing Sheets

PROCESS FOR EXTRACTION, PURIFICATION AND ENRICHMENT OF POLYPHENOLIC SUBSTANCES FROM WHOLE GRAPES, GRAPE SEEDS AND GRAPE POMACE

This application claims priority of Provisional Application No. 60/140,378 filed Jun. 22, 1999.

FIELD OF THE INVENTION

The present invention provides a novel process for the extraction, purification and concentration of polyphenolics from whole grapes, grape pomace and grape seeds. The liquid and powdered products of the present processes are particularly rich in polyphenolics, including anthocyanins, catechin monomers and their oligomers. These oligomers are frequently referred to as procyanidins in the field of polyphenol chemistry.

BACKGROUND OF THE INVENTION

Polyphenolic extracts from grape components have acquired special attention in the nutraceutical and food and beverage industries due to their widely publicized ability to function as antioxidants. The well known epidemiological studies conducted in France examined the protective effects of red wine consumption in reducing cardiovascular diseases. Such effects, described in the well-known "French Paradox" study, are strongly correlated to the presence of polyphenols in wine. Other studies indicate that red grape juice has antioxidant and platelet control activity comparable to that of red wine.

It is known in polyphenol chemistry that polyphenol compounds from vegetable sources can be extracted with aqueous solvents such as aqueous acetone, aqueous ethanol and aqueous methanol. Aqueous ethanol containing 50–80% ethanol is commonly utilized for such extractions.

It is also known that acetone and alcohols can be utilized to efficiently extract gallic acids, catechin monomers (i.e. catechin, epicatechin, epicatechin gallates), and oligomeric procyanidins from grape seeds. Extraction with acetone and alcohols yields oligomeric procyanidins with a degree of polymerization ("DP") of 2 to 7 and polymeric procyanidins with a DP of up to 16.

U.S. Pat. Nos. 3,435,407 and 4,698,360 disclose a method for the extraction of proanthocyanidins from pine bark, to the exclusion of the accompanying polymeric polyphenols (condensed tannins) comprising sodium chloride extraction and precipitation. These methods require repeated extraction with ethyl acetate. The ethyl acetate is then reduced by evaporation, and oligomeric procyanidins are precipitated by the addition of chloroform. The methods disclosed in these patents, however, are not commercially practicable or safe. These methods rely on solvent-solvent partition processes which require special handling, with explosion proof equipment and facilities. In addition, the resultant oligomeric bark extract commercial product may not be readily marketable as it may require label disclosure of the presence of solvent residues.

U.S. Pat. No. 5,484,594 is directed to a multistage process for preparing grape seed extract rich in procyanidolic oligomers. The '594 patent discloses extraction of seeds with 80% aqueous acetone, evaporation of the solvent and concentration of polyphenols. These steps are followed by refrigerated storage for 24 hours to precipitate polymeric procyanidins, and filtration. The method of '594 further includes ultrafiltration of the extract to remove high molecular weight substances and an additional ultrafiltration with tighter molecular cut off membranes to further minimize high molecular polymeric procyanidins. The ultrafiltration permeate is extracted repeatedly with ethyl acetate to remove catechin monomers. The extract is further extracted with ethyl acetate to exhaustion in order to extract all oligomeric procyanidins. The organic phase is concentrated under vacuum and the oligomers are precipitated by the addition of methylene chloride. The precipitate is centrifuged and dried at 50° C. under vacuum for 24 hours to purified powdered extract.

The practical utility of the multi-step solvent dependent process of the '594 patent is limited due to the acetone extraction required to remove unwanted polymeric procyanidins from the grape seed, removal of which then requires several additional steps, such as selective membranes and solvents. Also, solvent residues tend to remain in the dried extracts.

U.S. Pat. No. 5,912,363 relates to a method for extraction of proanthocyanidins from plant material. The '363 patent discloses heating an aqueous solid plant material mixture at temperatures of up to 350° F. under increased pressure and/or reduced oxygen, followed by membrane filtration, preferably ultrafiltration, to produce a permeate containing extracted proanthocyanidins. The extracted proanthocyanidins are then separated from the permeate by contacting the permeate with an adsorbent resin. All the examples are carried out at a temperature of 240° F., over the boiling point of water at atmospheric pressure.

The process disclosed in the '363 patent is characterized by both a limited practicality and a less than optimal purity of the proanthocyanidin extract. It is believed that the use of high temperature necessitates the use of membrane filtration, and limits the practical utility of this method.

OBJECTS AND SUMMARY OF THE INVENTION

The present invention provides a novel process that allows for extraction, purification and concentration of polyphenol substances from whole grapes, grape seeds and grape pomace without the need for membrane filtration. Aspects of several embodiments of the novel processes disclosed herein include hot water extraction; a dual pH treatment of the hot water extracts, and the uses of a copolymer of trimethylolpropane trimethacrylate ("TMPTMA"), commercially available as XAD-7HP®, as an adsorbent resin to maximize the concentration and purification of beneficial polyphenolic substances.

The processes of the present invention produce a highly concentrated polyphenol product by maximizing extraction of monomeric and oligomeric procyanidins and minimizing extraction of polymeric procyanidins. The instant invention does not require solvent extraction of the source materials, membrane filtration, or solvent-solvent partitioning. As such, the processes of the present invention are safer, simpler and higher-yielding than those previously known. The present invention is thus better-suited for large scale commercial/industrial and winery production than previously known methods.

The products produced by the instantly claimed processes may be used in foods, beverages and nutraceuticals as an antioxidant and to help lower the incidence of cardiovascular diseases; and in cosmetic preparations as an antioxidant. Antioxidant properties are beneficial across a wide range of applications. Thus, foods, beverages, dietary supplements, nutraceutical products and cosmetics containing the polyphenolic products of the instantly claimed processes may be produced. The highly concentrated polyphenol product of the whole grape processes of the present invention is also rich in anthocyanins and oligomeric procyanidins. The whole grape extract, in liquid or powder form, may be used as a colorant in food products, beverages, cosmetics and dietary supplements.

BRIEF DESCRIPTION OF THE DRAWINGS

Chromatographic conditions: Column Phenomenex Prodigy 5$\mu$ ODS (3) 100A, 250×4.6 mm column with a Phenomenex Prodigy 5$\mu$ ODS (3) 100A, 30×4.6 mm guard column at 30° C. Solvent A: 2% acetic acid, B: 80% acetonitrile, 0.4% acetic acid; 3 minutes at 100% A, 3 min linear gradient to 4% B, 9 min linear gradient to 10% B, 15 min linear gradient to 15% B, 20 min linear gradient to 23% B, 10 min linear gradient to 25%, 6 min linear gradient to 30% B, 14 min linear gradient to 50% B, 3 min linear gradient to 80% B, followed by a 2 min linear gradient to original starting conditions. The column was re-equilibrated to the starting solvent for 20 min between runs. Flow rate 1.0 mL/min. Injection volume 25 $\mu$L

DETAILED DESCRIPTION OF THE INVENTION

As used throughout this specification, "oligomeric procyanidins" refers to procyanidins having a degree of polymerization ("DP") of 2 to about 7; "polymeric procyanidins" refers to procyanidins having a degree of polymerization of 8 or greater; "aqueous solvent" (e.g. "aqueous ethanol") refers to a solution of water and solvent; "X % aqueous solvent"(e.g. "80% aqueous ethanol") refers to a solution containing X % (v/v) of solvent. Thus, 80% aqueous ethanol contains 20% water and 80% ethanol (v/v).

The instant invention provides new processes for the extraction, purification and concentration of polyphenolic substances from grapes, grape seeds and grape pomace. The methods of the present invention are more commercially practicable than currently known methods.

To extract grape seeds, grape seeds, dry or fresh, are heated with hot water for a time sufficient to extract most of the polyphenols. Temperatures of 140–212° F. may be employed, preferably 160°–212° F., more preferably 180°–212° F., yet more preferably 190°–212° F., for a period of 1–6 hours. Temperatures over 212° F. should be avoided.

The time of heating may be varied in relation to the temperature used. Generally, lower temperatures require longer extraction times. In one embodiment, the seeds are boiled at about 212° F. for a period of two hours, resulting in the extraction of the desirable monomeric phenols, including gallic acid, catechin, epicatechin and epicatechin gallates and oligomeric procyanidins, with a DP of 2 to 7, while minimizing extraction of polymeric procyanidins including condensed tannins.

The crude grape seed-water extract can be separated from spent seeds by draining over metal screens. The extract is then cooled and treated with any suitable commercially available pectolytic enzyme, such as Pectinex® Ultra SP-L manufactured by Novo Nordisk, to break down cell wall constituents. Preferably, the seed water extract is enzyme-treated for a period of two hours at 80°–120° F. Alternatively, the seed-water extract may be enzyme-treated for 7–14 days or longer at about 40°–50° F.

The resulting highly turbid seed extract is acidified with an acid, preferably a mineral acid, more preferably with sulfuric acid, to a pH of approximately 1.5–2.5 and allowed to react from 1 to 48 hours. The acidified extract is cooled for up to several weeks to allow for macromolecules, including proteins and other polysaccharides, to settle. The cooled acidified extract is then filtered using diatomaceous earth to yield a clarified seed extract. Other filter aids such as perlite, may also be used.

In one embodiment; the acidified extract may be neutralized with a base, preferably an alkali metal base, more preferably with sodium or potassium hydroxide to a pH of about 4.0–6.0 and allowed to react for 10 minutes to several days. The dual pH treatment results in compact flocculated solids and a clear seed extract. Where such a dual pH treatment is utilized, the order of the pH treatments may be reversed. The dual pH treatment is an unique feature of this process. Dual pH treatment results in better flocculation of macromolecules including proteins and other polysaccharides, leaving the grape seed phenols in clear solution. This solution can optionally be filtered through diatomaceous earth or an equivalent filter aid 30 to 60 minutes after flocculation.

3–25 bed volumes of the clarified seed extract, depending upon the phenol concentration, is adsorbed on a column containing an adsorbent selected from the group consisting of styrene divinyl benzene copolymer, including but not limited to XAD-16® a polymer sold by Rohm & Haas, and a polymer of trimethylolpropane trimethacrylate ("TMPTMA"), including but not limited to XAD-7HP® (also known as S877) also manufactured by Rohm & Haas. XAD-7HP® is the adsorbent resin of choice for this application.

XAD-7HP® is preferred since it allows for high specific loading of seed extract monomers and oligomers and has practically no affinity for other seed components such as organic acids, reducing sugars, minerals, proteins, amino acids, or processing aids such as sulfuric acid and potassium hydroxide used to assist in clarification of crude seed extract.

The effluent is discarded, and the adsorbent resin column containing adsorbed proanthocyanidins is rinsed with sufficient volume of water to further remove entrapped/adhering solutes from the resin. The adsorbed monomers and oligomers are eluted from the column with a sufficient volume of 50–95% aqueous ethanol, preferably 1–3 bed volumes. Other solvents, including acetone or methanol, may be used to elute the adsorbed polyphenols from the resin.

The eluant, a highly concentrated solution of proanthocyanidin monomers and oligomers, is subjected to vacuum evaporation (distillation) to remove solvent and the residue is taken up in a small volume of water. This aqueous extract has a very high concentration of monomers and oligomers (5–45% by weight) with an appearance of dark brown liquid.

The aqueous solution can be vacuum dried, spray dried or freeze dried to a free flowing powder with greater than 85% of the total phenols containing monomeric (gallic acid, catechin, epicatechin and epicatechin gallate) and oligomeric procyanidins. This free flowing powder is freely soluble in water.

To extract grape pomace, the pomace is heated with hot to boiling water for a time sufficient to extract most of the polyphenols. Temperatures of 140°–212° F. may be employed, preferably 160°–212° F., more preferably 160°–180° F., most preferably 170° F., with sufficient water for a period of 1–6 hours, preferably 1–3 hours. The time of heating may be varied in relation to the temperature used. Generally, lower temperatures require longer extraction times. In one embodiment, approximately 1 part by weight of grape pomace is extracted with 3 to 5 parts of water in a heating vessel for 1 to 6 hours at about 140°–212° F. The extract is separated from grape residue and treated with any suitable commercially available pectolytic enzyme for a sufficient time and at an appropriate temperature to break down cell wall constituents, preferably Pectinex® Ultra SP-L for 2 hours at 100°–120° F. or 7–14 days at 40°–50° F. The extract is filtered using diatomaceous earth. Other filter aids, such as perlite, may also be utilized.

3–25 bed volumes of the clear pomace extract is adsorbed on a bed of XAD-7HP® or XAD-16® adsorbent resin and the column effluent is discarded. The resin is slowly rinsed with 1–5 bed volumes of water to remove entrapped/adhering water soluble impurities. The adsorbed polyphenols, which include monomeric and oligomeric procyanidins, and anthocyanins (if red grape pomace is used) are eluted from the column with a suitable amount of solvent, preferably 1 to 5 bed volumes of 50–95% ethanol. The solvent is evaporated from the eluant and the residue is taken up with water. The resulting solution is spray dried to a powder which contains 50–80% total monomeric and oligomeric procyanidins and anthocyanidins (if red grape pomace is used) by weight and is freely soluble in water.

To extract whole grapes, dark red grapes are crushed and heated in a suitable vessel in the presence of a pectolytic enzyme to a temperature range of about 120°–180° F., preferably 130°–150° F., most preferably 140° F., for a period of 1–6 hours, preferably 1–2 hours. The time of heating may be varied in relation to the temperature used. The aqueous material, rich in grape sugars, polyphenolics (flavanols, flavonols, anthocyanins and cinnamate derivatives), organic acids and minerals is separated from insoluble grape solids with a perforated screen. The remaining solids are further pressed with continuous presses to recover a liquid relatively rich in polyphenols. All liquid portions are combined and chilled to about 30°–35° F. for a period of several days to settle insoluble solids and precipitate tartrates. The supernatant liquid is filtered to clarity through diatomaceous earth. Other filter aids, such as perlite, may also be utilized.

The clarified extract is adsorbed on a column of adsorbent resin XAD-7HP®. The column effluent may be used as a juice, or may be fermented to wine. The column is rinsed with 1–5 bed volumes of water to remove adhering sugars, acid and minerals. The adsorbent resin is eluted with sufficient solvent to recover all the adsorbed polyphenols from whole grape extract, preferably, 1–5 bed volumes of 50–95% ethanol. Solvent is removed by evaporation and the residue, a polyphenol rich liquid is spray dried to a free flowing powder which contains 50–75% total polyphenols by weight and is freely soluble in water.

The present invention will now be further explained in the following examples, which further describe, but do not limit the scope of the invention.

EXAMPLE 1

Grape Seed Extraction and Purification

Eight batches of seed extract are prepared as follows. For each batch, 150 lbs. of dried red grape seeds were mixed with 43.2 gallons of water. Each batch is heated to boiling in a steam jacketed kettle and held at boiling temperature for two hours under vigorous agitation. At the end of two hours, free liquid is drained and 7.2 gallons of fresh water is added to the cooked seeds, mixed and then drained. This rinse step is repeated two additional times to facilitate improved recovery. The volume of crude extract collected ranged from 57 to 69 gallons and the total phenolics content is determined by the Folin-Ciocalteau colorimetric method (Singleton, V. L. and Rossi, J. L., *Colorimetry of total phenolics with phosphomolybdic—phosphotungstic acid reagents*, Am. J. Enol. Vitic, 16:144–158 (1965)), according to which the phenolics, in the presence of alkaline and heat, are oxidized by the Folin-Ciocalteau reagent. Such reduced reagent forms a blue colored product whose absorbance is read on a spectrophotometer. The total phenolics content ranged from 6,640 to 11,680 ppm, equivalent to the extraction of 2.5–4.4 lbs. of phenols per 100 lbs. of seed. The relative percent phenols as determined by an HPLC method is:

| | Relative Percent Phenols (HPLC) |
|---|---|
| monomers | 11.3–12.3% |
| oligomers | 67.5–70.4% |
| polymers | 17.4–21.1% |

The extracts are cooled to 100°–120° F., treated with a pectolytic enzyme, and allowed to sit overnight. Next, sulfuric acid is added to reduce the pH of the extract to 2.0. The extracts are stored at 40° F. for 10–20 days and allowed to settle. Subsequently, the extracts are decanted and filtered through diatomaceous earth. 350–400 L of the so-clarified extract is passed slowly through a 25 liter column of XAD-7HP® adsorbent resin at the rate of 62.5 L per hour. At the completion of the adsorption cycle, 80–100 mg of phenols are absorbed per mL of resin. Non-phenolics are washed off the column with 25 L of water, then the phenols are eluted using 25 liters of 95% ethanol at the rate of 25 L per hour followed by an additional water rinse of 25 L. The volume of the phenol-containing eluant is approximately 31 liters. This procedure is repeated until all of the clarified extract is similarly processed.

The following table illustrates results of a component analysis of the clarified extract and the eluant and demonstrates that minerals, sugars and organic acids in the extract pass through the column and are not absorbed. Mineral content is determined by atomic adsorption, sugar content by HPLC, and organic acid content by capillary electrophoresis methods.

| | Clarified Extract Before Adsorption/Elution | Eluant |
|---|---|---|
| residual sugar | 0.349 g/100 mL | ND |
| Na | 563 mg/L | 9 mg/L |
| K | 67 mg/L | ND |
| malic | 238 mg/L | ND |
| tartaric | 1052 mg/L | ND |
| sulfate | 1866 mg/L | ND |
| succinic | 97 mg/L | ND |
| acetic | 129 mg/L | ND |

Alcohol is removed from the eluted extract under vacuum, leaving a residue which is then spray dried. Yield of grape seed extract powder for the eight batches of seeds ranged from 1.7 to 2.4 lbs. per 100 lbs. of original dry seeds. Composition of the dry powders is found to be as follows:

| | |
|---|---|
| total phenols content | 89.7–93.3% |
| relative % monomers | 12.0–14.0% |
| relative % oligomers | 72.7–74.9% |
| relative % polymers | 11.0–15.2% |

EXAMPLE 2

Grape Seed Extraction and Purification—Dual pH Treatment

In a manner similar to that described in Example 1, 7,100 lbs. of dried red grape seeds are extracted in about 2,000 gallons of boiling water for two hours. After de-watering and rinsing the seeds, 2,000 gallons of crude extract are collected. The composition of this extract is determined to be as follows:

| | |
|---|---|
| total phenols content | 13,040 mg/L |
| relative % monomers | 10.9% |
| relative % oligomers | 75.2% |
| relative % polymers | 13.9% |

Figure 1A:
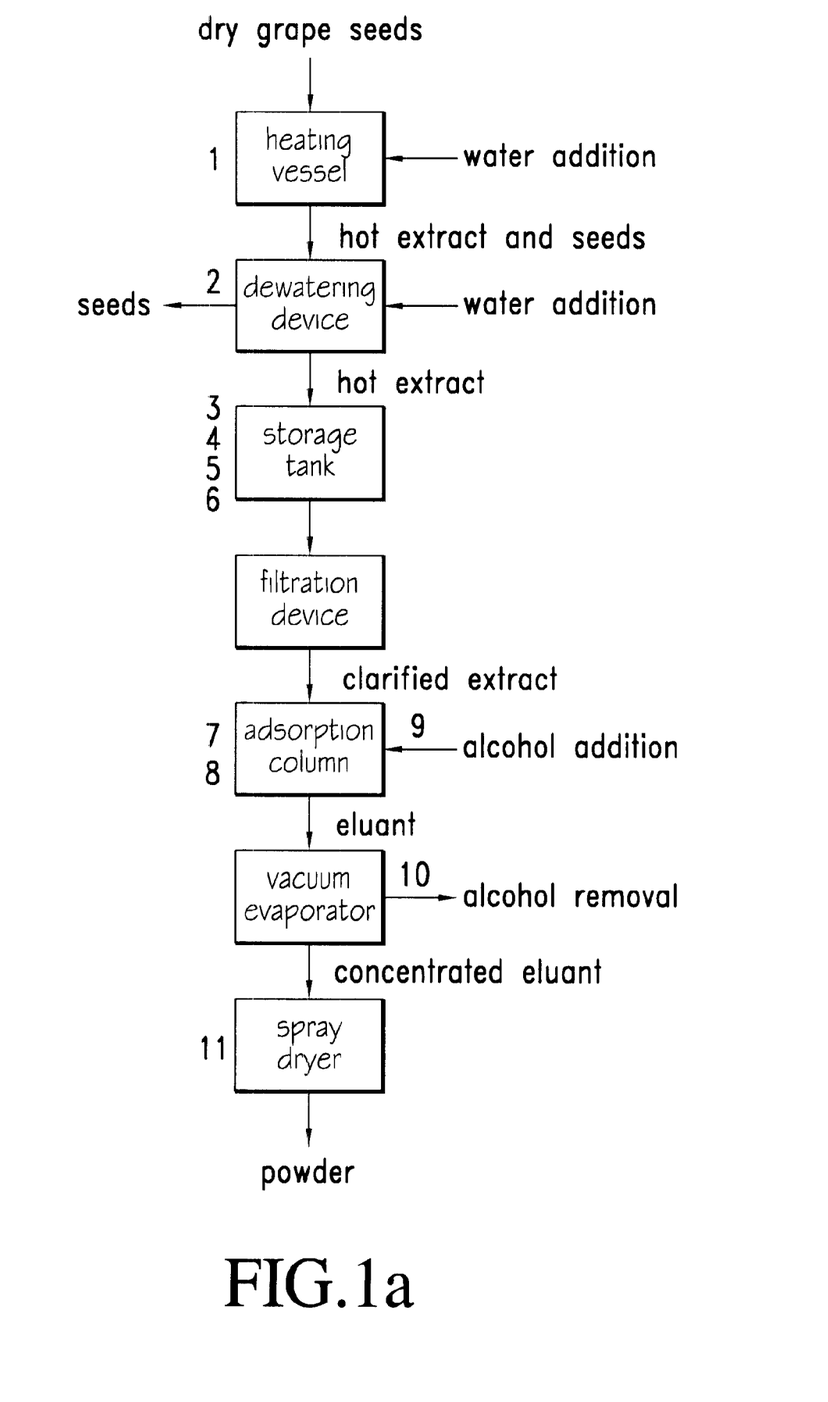
FIG. 1a. illustrates the steps for extraction, purification and enrichment of proanthocyanidin oligomers from grape seeds.
Figure 1B:
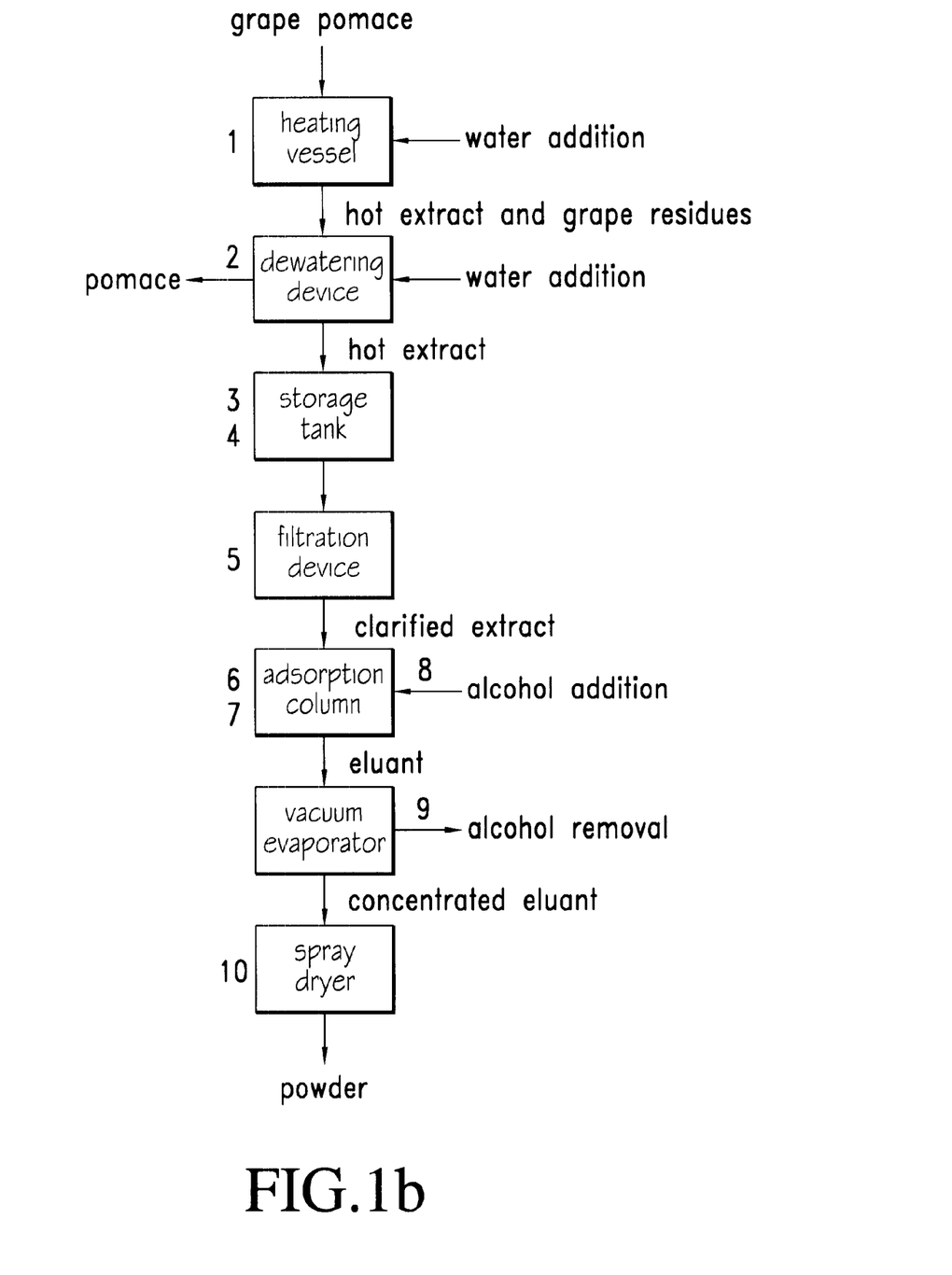
FIG. 1b. illustrates the steps for extraction, purification and enrichment of proanthocyanidin oligomers from grape pomace.
Figure 1C:
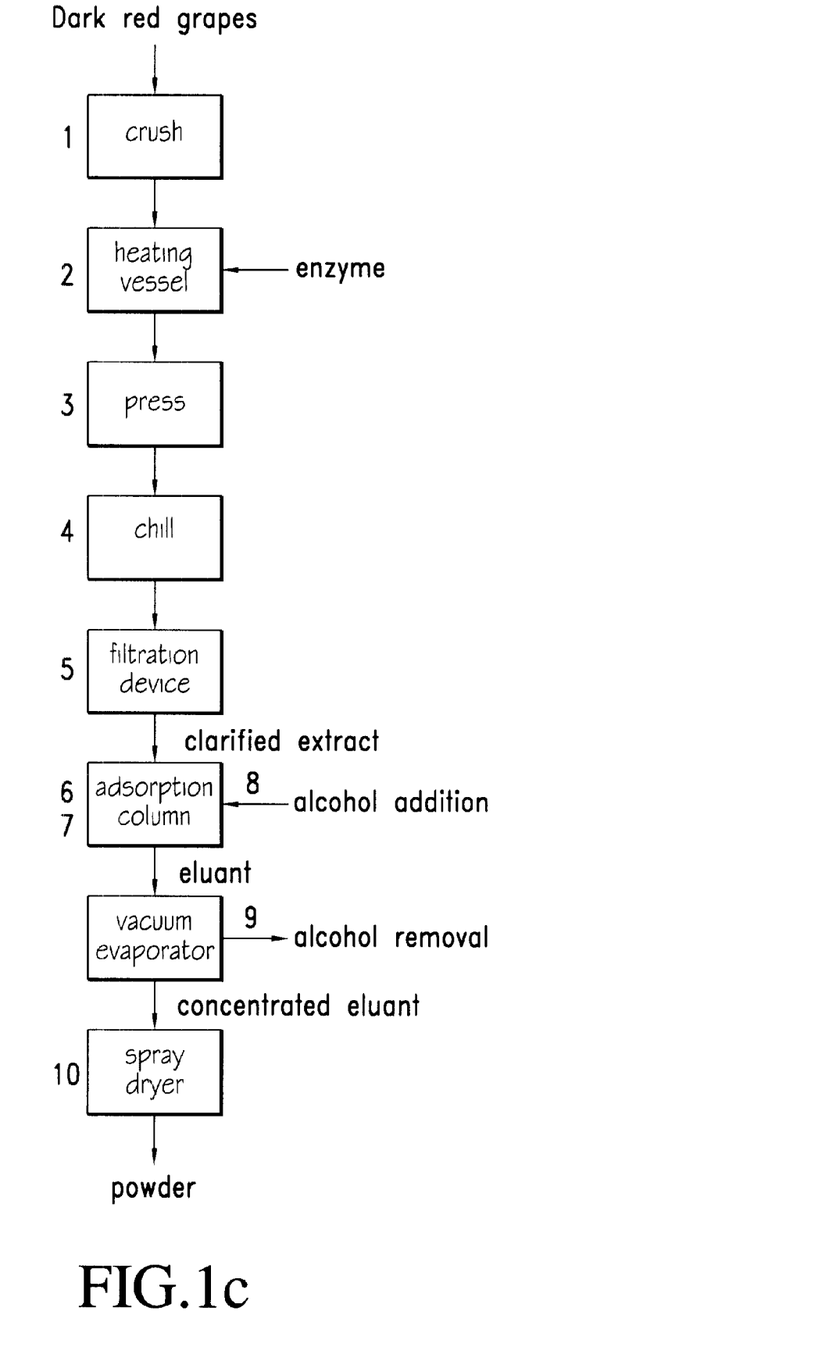
FIG. 1c. illustrates the steps for extraction, purification and enrichment of extractable polyphenols from dark red grapes.
Figure 2A:
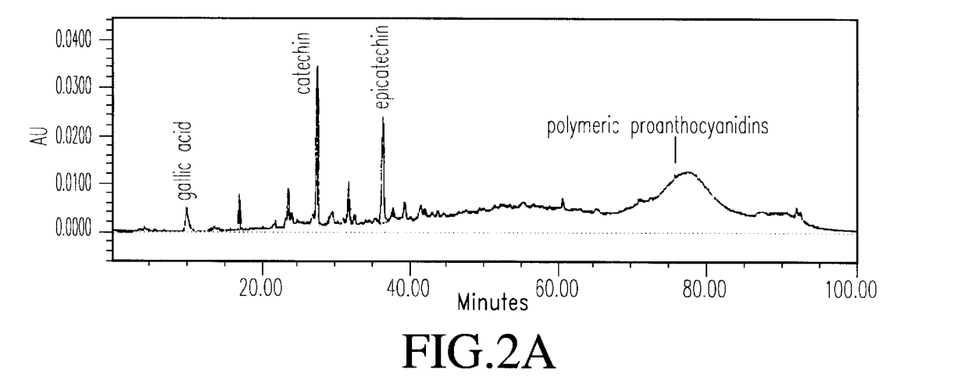
FIG. 2A is a high pressure liquid chromatogram of the product resulting from extraction of grape seeds with 75% ethanol.
Figure 2B:
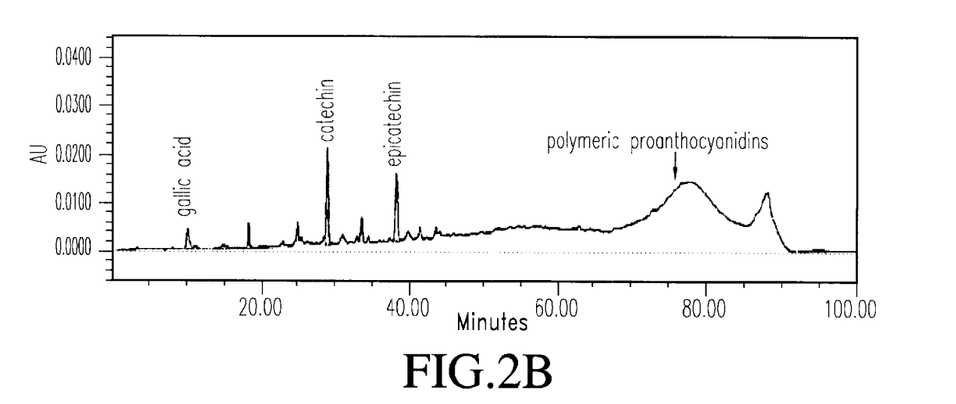
FIG. 2B is a high pressure liquid chromatogram of the product resulting from extraction of grape seeds with 50% aqueous acetone.
Figure 2C:
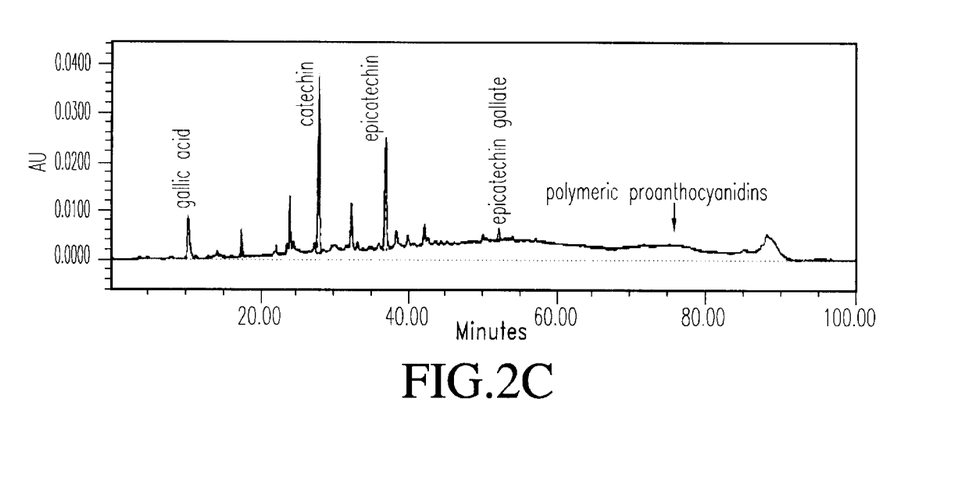
FIG. 2C is a high pressure liquid chromatogram of the product resulting from extraction of grape seeds with boiling water.
Figure 3:
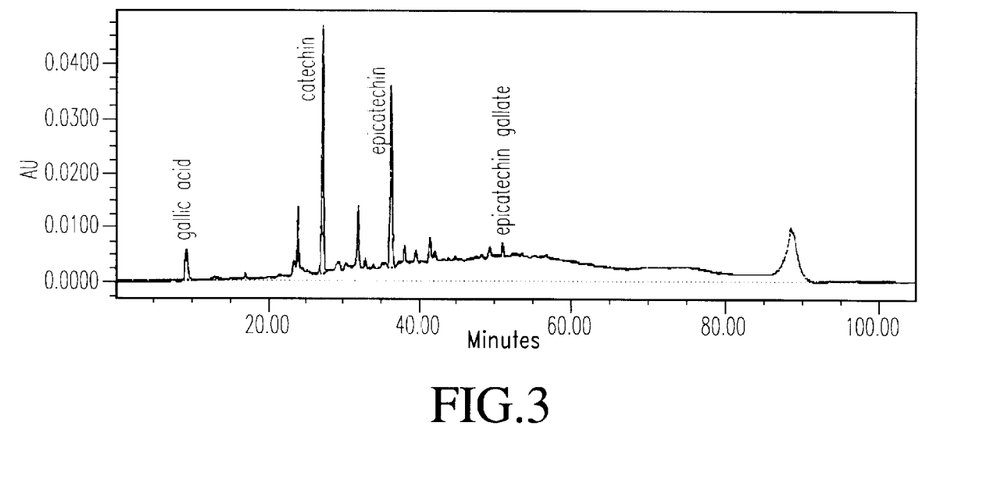
FIG. 3 is a high pressure liquid chromatogram of purified grape seed extract powder prepared by adsorption elution.

The extract is cooled to 100–120° F. and treated overnight with pectolytic enzymes. Next, the pH of the extract is reduced to 2.5 followed by chilling to 40° F. After three weeks, the pH is increased to 4.5 with potassium hydroxide which causes a rapid flocculation and sedimentation of the insoluble and colloidal substances. The extract is decanted and filtered, adsorbed on an XAD-7HP® resin as previously described and processed into a spray dried grape seed extract powder. Analyses of this powder confirmed a high degree of purification compared to the raw extract. The weight of powder recovered is 2.29 lbs. per 100 lbs. of original dry seeds. A HPLC Chromatogram of this purified powder is shown in FIG. 3. The chromatogram and tabulated data show a large proportion of oligomeric procyanidins with relatively small proportion of polymeric procyanidins is produced by the method of the instant invention.

| Component | Clarified Extract | Concentrated Eluant | Powder |
|---|---|---|---|
| total phenols | 12,660 mg/L | 63,000 mg/L | 94.2% |
| relative % monomers | 11.4% | | 11.7% |
| relative % oligomers | 74.9% | | 74.3% |
| relative % polymers | 13.7% | | 14.0% |
| Na | 30 mg/L | ND | |
| K | 1,826 mg/L | 59 mg/L | |
| Ca | 226 mg/L | 26 mg/L | |
| Cu | 0.205 mg/L | 1.2 mg/L | |
| Fe | 1.2 mg/L | 3.44 mg/L | |
| Mg | 119 mg/L | 21 mg/L | |
| malic | 311 mg/L | 51 mg/L | |
| tartaric | 1,029 mg/L | ND | |
| sulfate | 1,494 mg/L | ND | |
| succinic | 110 mg/L | ND | |
| acetic | 387 mg/L | ND | |
| lactic | 19 mg/L | ND | |
| total organic acids | | | ND |
| residual sugars | | | ND |
| total minerals | | | 3,550 mg/kg |

EXAMPLE 3

Grape Pomace Extraction and Purification

One part by weight Zinfandel grape pomace (skins and seeds) are combined with five parts potable water. This mixture is stirred vigorously for one hour at 170° F. after which the liquid is drained and the pomace pressed. Extract streams are combined and chilled to 40° F. A pectolytic enzyme is added and sufficient time is allowed for depectinization to reach completion. After the extract has settled and become clear it is decanted and filtered through diatomaceous earth.

Two liters of filtered extract is adsorbed on a 100 mL XAD-7HP® adsorbent resin column at the rate of 2.5 bed volumes per hour, rinsed with 100 mL of water and eluted with one bed volume of 75% ethanol. 112 mL of eluant are collected. The eluant is stripped of alcohol under vacuum and dried overnight in a vacuum oven. 5.89 grams of powder are collected. The composition of extract, eluant and powder appear in the following table:

| | Extract | Eluant | Powder |
|---|---|---|---|
| total phenols | 2,460 mg/L | 39,600 mg/L | 76.3% |
| relative % monomers | | | 10.2% |
| relative % oligomers | | | 77.4% |
| relative % polymers | | | 12.4% |
| residual sugars | ND | ND | |
| Na | 18 mg/L | ND | |
| K | 1,138 mg/L | 313 mg/L | |
| Ca | 147 mg/L | 30 mg/L | |
| Cu | 0.88 mg/L | 0.65 mg/L | |
| Fe | 4.49 mg/L | 2.55 mg/L | |
| Mg | 106 mg/L | 39 mg/L | |
| malic | 344 mg/L | 179 mg/L | |
| tartaric | 4,439 mg/L | 1,381 mg/L | |
| sulfate | 105 mg/L | ND | |
| succinic | 103 mg/L | ND | |
| acetic | 125 mg/L | ND | |
| lactic | 75 mg/L | ND | |

EXAMPLE 4

Grape Seed Extraction and Purification—Dual pH Treatment 1200 grams of dried Rubired seeds is extracted with 2.88 liters of boiling water in a manner as described in Example 1. After rinsing the seeds with 0.50 L of water three times the extract is cooled to 114° F. and treated with 200 ppm pectolytic enzyme for two hours. Next, sulfuric acid is added to reduce the pH to 2.0. The acidified extract is held at room temperature for one hour followed by addition of potassium hydroxide to raise the pH to 4.5. Immediately upon the final pH adjustment a heavy flocculation is seen to form which rapidly sediments, leaving a clear supernatant. The phenolic composition of the supernatant is as follows:

|  | Raw Extract | After Enzyme Treatment | After treatment at pH 2.0 | After treatment at pH 4.5 |
| --- | --- | --- | --- | --- |
| total phenols (mg/L) | 8,400 | 8,575 | 8,575 | 7,950 |
| relative % monomers | 11.2 | 11.2 | 10.9 | 10.8 |
| relative % oligomers | 73.8 | 73.1 | 73.0 | 73.9 |
| relative % polymers | 15.5 | 15.7 | 16.1 | 15.3 |

The supernatant is then allowed to settle for 48 hours, decanted and filtered. One liter of the filtered extract is adsorbed on a 100 mL column of adsorbent resin XAD-7HP® at the rate of 2.5 bed volumes per hour, rinsed with 100 mL of water and eluted with 75% ethanol in the manner previously described. 120 mL of eluant is collected. A portion of the eluant is stripped of alcohol under vacuum and dried overnight in a vacuum oven. Analysis of the dried eluant powder yielded the following analyses:

| % total phenols | 93.6% |
| --- | --- |
| relative % monomers | 10.9% |
| relative % oligomers | 74.0% |
| relative % polymers | 15.1% |

EXAMPLE 5

Grape Seed Extraction and Purification—Dual pH Treatment 1,200 grams of dried grape seeds comprised of a blend of Muscat and Chardonnay white varieties is extracted in 2.88 L of boiling water as previously described. After three rinses of 0.50 liters each, the extract is cooled to 100° F. and treated with pectolytic enzyme Pectinex® Ultra SP-L for two hours. Next, sulfuric acid is added to reduce the pH to 2.0 followed by storage overnight at room temperature. Following overnight storage, potassium hydroxide is added to increase the pH to 4.5 whereupon the typical instantaneous flocculation and precipitation is seen to occur. After an additional 72 hours, the clarified supernatant is decanted, filtered through diatomaceous earth and adsorbed on XAD-7HP® resin. 1,000 mL of extract are adsorbed on a 100 mL column at the rate of 4.2 mL/minute. After applying a 100 mL rinse with potable tap water, the column is eluted using 100 mL of 95% ethanol and 156 mL of eluant is collected. A sample of the eluant is stripped of alcohol and dried overnight in a vacuum oven. The analysis of the resulting powder, phenolics profile and of the raw, clarified extract is set forth in the following table:

|  | Clarified Extract | Dried Powder |
| --- | --- | --- |
| total phenols | 10,840 mg/L | 87.19% |
| relative % monomers | 3.6% | 3.8% |
| relative % oligomers | 69.8% | 70.0% |
| relative % polymers | 26.7% | 26.2% |

EXAMPLE 6

Whole Grape Extract and Purification 2000 lbs. of dark whole grapes of a red hybrid variety are heated to 130° F. for 6 hours in a stainless steel tank fitted with a heat exchanger. The liquid is separated from the grape solids and the residue pressed to recover additional liquid. The liquids are combined and depectinized using pectolytic enzyme. Approximately 180–200 gallons of juice liquid are obtained at about 22.0 brix soluble solids. Approximately 800 mL of this juice from whole grapes is filtered through diatomaceous earth and adsorbed on a 100 mL column of XAD-7HP®. The column is rinsed with 100 mL of water and eluted with 100 mL of 95% ethanol. Alcohol is removed from the eluted extract under vacuum, which is then dried overnight in a vacuum. Approximately 3.52 g. of powder is recovered. Analyses of the whole grape liquid extract, eluant and power are as follows:

|  | Grape Extract | Eluant | Powder |
| --- | --- | --- | --- |
| total phenols | 4,475 mg/L | 19,800 mg/L | 56.2% |
| total anthocyanins | 0.29 g/100 g | 1.32 g/100 g | 35.2% |
| color value | 0.32 | — | 38.3 |
| residual sugar | — | — | ND |
| organic acids | — | — | ND |
| total minerals | — | — | 1.23% |

The present process results in a powder having a very high phenol concentration in which anthocyanins constitute approximately 63% of the total polyphenols. The color value of a 1% solution in pH 3.2 buffer measured at 520 nm of this powder has an extinction coefficient of 38.3. The product of this process may be used as a high polyphenol-content powder for nutraceuticals as well as a colorant with a high color value for coloring foods, beverages and cosmetics.

EXAMPLE 7

Grape Seed Extraction and Purification 68 kg of dry mixed variety grape seeds are extracted with 163.5 L of boiling water in a manner similar to that described in Example 1. After two hours, the seeds are drained and rinsed with 81.8 L of water and again drained. The crude extract is cooled to 120° F., treated with 200 ppm pectolytic enzyme and held overnight at room temperature. The pH of the extract is reduced to 2.0 and then stored for seven days at 40° F. The extract is decanted and filtered through diatomaceous earth. 5.35 L of the so-clarified extract is adsorbed on a 550 mL bed volume column of adsorbent resin XAD-16® at the rate of 2.5 bed volumes per hour. The column is rinsed with one bed volume of water and eluted with 0.55 L of 95% ethanol; 550 mL of eluant are collected. A sample of the eluant is dried in a vacuum oven overnight and the powder recovered is equivalent to 2.28 grams per 100 grains of original dry seeds. Composition of the various extract fractions was found to be as follows:

|  | Clarified Extract | Column Eluant | Dry Powder |
|---|---|---|---|
| total phenols | 10,425 mg/L | 69,900 mg/L | 86.5% |
| relative % monomers | 11.3% |  | 10.5% |
| relative % oligomers | 73.8% |  | 73.9% |
| relative % polymers | 14.9% |  | 15.6% |
| residual sugars | 0.93 g/100 mL | ND |  |
| sodium | 64 mg/L | ND |  |
| potassium | 511 mg/L | ND |  |
| malic acid | 263 mg/L | ND |  |
| tartaric acid | 623 mg/L | ND |  |
| sulfate | 1,897 mg/L | ND |  |
| citric | 84 mg/L | ND |  |
| succinic acid | 54 mg/L | ND |  |
| acetic acid | 428 mg/L | ND |  |

EXAMPLE 8

Grape Pomace Extraction and Purification

In a manner as described in Example 3, Zinfandel grape pomace is extracted, drained, depectinized, clarified and filtered through diatomaceous earth. 3 L of clarified extract is passed though a 100 mL column of adsorbent resin XAD-16® at the rate of 250 mL per hour followed by a 100 mL of rinse with water. The column is eluted with 100 mL of 95% alcohol. The eluant is dried overnight in a vacuum oven. The yield of powder is 2.8 grams per 100 grams of original pomace.

|  | Clarified Extract | Eluant | Dry Powder |
|---|---|---|---|
| total phenols | 1,187 mg/L | 28,225 mg/L | 67.5% |

EXAMPLE 9

Grape Seed Extraction and Purification—Dual pH Treatment 1200 grams of dried Rubired seeds is extracted with 2.88 liters of boiling water in a manner as described in Example 1. After rinsing the seeds with 0.50 L of water three times, the extract is cooled to 100° F. and treated with 200 ppm pectolytic enzyme for two hours. Next, potassium hydroxide is added to increase the pH to 5.0. The depectinized extract is held at room temperature for one hour followed by addition of sulfuric acid to reduce the pH to 2.0. Immediately upon the final pH adjustment a heavy flocculate forms which rapidly sediments, leaving a clear extract supernatant. The phenolic composition of the extract is as follows.

|  | Enzyme Treated Extract | Dual pH (5.0/2.0) Treated Extract |
|---|---|---|
| total phenols (ppm) | 6,400 | 6,600 |
| relative % monomers | 14.3 | 14.6 |
| relative % oligomers | 71.4 | 71.6 |
| relative % polymers | 14.4 | 13.8 |

What is claimed is:

1. A process for preparation of a purified polyphenol extract of grape seeds which comprises the step of:

(a) extracting grape seeds with water at a temperature of about 140°–212° F. to obtain a grape seed extract,
   (b) subjecting said grape seed extract to a dual pH treatment.

2. The process of claim 1 in which the dual pH treatment of step (b) comprises acidification of said grape seed extract to a pH of 1.5 to 2.5, and further comprising the steps of:
   (a1) treating said grape seed extract with a pectolytic enzyme; and
   (c) treating the grape seed extract with an adsorbent resin to obtain a substantially purified polyphenol extract.

3. The process of claim 2 further comprising the steps of:
   (d) filtering said grape seed extract to yield a filtered polyphenol extract.

4. The process of claim 2, wherein the adsorbent resin is a TMPTMA polymer resin.

5. The process of claim 1, wherein said dual pH treatment comprises subjecting said grape seed extract to a basification process by raising the pH of said grape seed extract to between 4.0 to 6.0.

6. The process of claim 1, wherein in step (a), said grape seeds are heated at about 140°–212° F. in water for about 1–6 hours to obtain grape seed extract.

7. The process of claim 1, wherein in step (a), said grape seeds are extracted with water at a temperature of about 160°–212° F.

8. The process of claim 1, wherein in step (a), said grape seeds are extracted with water at a temperature of about 180°–212° F.

9. The process of claim 1, wherein in step (a), said grape seeds are extracted with water at a temperature of about 190°–212° F.

10. A purified polyphenol extract produced according to the process of any of claims 1–3, 5 or 4.

11. A purified polyphenol extract produced according to the process of any of claims 1–3, 5 or 4 wherein the concentration of monomeric and oligomeric procyanidins is about 5–45% by weight.

12. A food product comprising a purified polyphenol extract of claim 11.

13. A beverage comprising a purified polyphenol extract of claim 11.

14. A cosmetic product comprising a purified polyphenol extract of claim 11.

15. A dietary supplement comprising a purified polyphenol extract of claim 11.

16. A nutraceutical product comprising a purified polyphenol extract of claim 11.

17. The process of any of claims 1–3, 5 or 4 further comprising drying of said grape seed extract to obtain a free flowing powder containing monomeric and oligomeric procyanidins.

18. A free flowing powder produced according to claim 17.

19. A free flowing powder produced according to claim 17 comprising more than 85% by weight polyphenols.

20. A food product comprising a free flowing powder of claim 19.

21. A beverage product comprising a solution or suspension of a free flowing powder of claim 19.

22. A cosmetic product comprising a free flowing powder of claim 19.

23. A dietary supplement comprising a free flowing powder of claim 19.

24. A nutraceutical product comprising a free flowing powder of claim 19.

25. A process for preparation of a purified polyphenol extract of grape pomace which comprises the step of:

(a) extracting said grape pomace with water at a temperature of about 140°–212° F. to obtain a grape pomace extract, and (b) subjecting said grape pomace extract to a dual pH treatment.

26. The process of claim 25 in which the dual pH treatment of step (b) comprises acidification of said grape pomace extract to a pH of 1.5 to 2.5 and further comprising the steps of:

(a1) treating the grape pomace extract with a pectolytic enzyme; and (c) treating the grape pomace extract with an adsorbent resin to obtain a substantially purified polyphenolic extract.

27. The process of claim 26, wherein the adsorbent resin is TMPTMA polymer resin.

28. The process of claim 25, wherein in step (a), said grape pomace is heated in water at a temperature of about 160°–212° F.

29. The process of claim 25, wherein in step (a), said grape pomace is heated in water at a temperature of about 160°–180° F.

30. The process of claim 25, wherein said grape pomace is heated in water at a temperature of about 170° F. for about 1–3 hours.

31. A purified polyphenol extract produced according to the process of any of claims 25, 26 or 27.

32. A food product comprising a purified polyphenol extract of claim 31.

33. A beverage comprising a purified polyphenol extract of claim 31.

34. A cosmetic product comprising a purified polyphenol extract of claim 31.

35. A dietary supplement comprising a purified polyphenol extract of claim 31.

36. A nutraceutical product comprising a purified polyphenol extract of claim 31.

37. The process of any of claims 25, 26 or 27 further comprising drying of said grape pomace extract to obtain a free flowing powder containing monomeric and oligomeric procyanidins.

38. A free flowing powder produced according to claim 37.

39. A free flowing powder produced according to claim 37 comprising about 50–80% polyphenols by weight.

40. A food product comprising a free flowing powder of claim 39.

41. A beverage product comprising a solution or suspension of a free flowing powder of claim 39.

42. A cosmetic product comprising a free flowing powder of claim 39.

43. A dietary supplement comprising a free flowing powder of claim 39.

44. A nutraceutical product comprising a free flowing powder of claim 39.

45. A process for the preparation of a purified polyphenol extract of dark red grapes which comprises the step of:

(a) subjecting said dark red grapes to hot water treatment at a temperature of about 120°–180° F. to obtain a grape extract, (b) subjecting said grape extract to a dual pH treatment.

46. The process of claim 45 in which the dual pH treatment of step (b) comprises acidification of grape extract to a pH of 1.5 to 2.5 and further comprising the steps of:

(a1) treating said grape extract with a pectolytic enzyme; and (c) treating the grape extract with an adsorbent resin to obtain a substantially purified polyphenol extract.

47. The process of claim 46, wherein the adsorbent resins is a TMPTMA polymer resin.

48. The process of claim 46, wherein in step (a), said dark red grapes are heated in water at a temperature of about 130°–150° F. for about 1–2 hours.

49. A purified polyphenol extract made by the process of any of claims 45, 46 or 47.

50. Colorant for food products comprising a purified polyphenol extract of claim 49.

51. Colorant for beverages comprising a purified polyphenol extract of claim 49.

52. Colorant for cosmetics comprising a purified polyphenol extract of claim 49.

53. Colorant for dietary supplements comprising a purified polyphenol extract of claim 49.

54. A food product comprising a purified polyphenol extract of claim 49.

55. A beverage comprising a purified polyphenol extract of claim 49.

56. A cosmetic product comprising a purified polyphenol extract of claim 49.

57. A dietary supplement comprising a purified polyphenol extract of claim 49.

58. A nutraceutical product comprising a purified polyphenol extract of claim 49.

59. The process of any of claims 45, 46 or 47 further comprising drying of said grape extract to obtain a free flowing powder containing monomeric and oligomeric procyanidins, anthocyanins, flavanols and cinnamic acids.

60. A free flowing powder produced according to claim 59.

61. A free flowing powder produced according to claim 59 comprising about 50–75% polyphenols by weight.

62. A beverage product comprising a solution or suspension of a free flowing powder of claim 53.

63. A cosmetic product comprising a free flowing powder of claim 61.

64. A dietary supplement comprising a free flowing powder of claim 61.

65. A nutraceutical product comprising a free flowing powder of claim 61.

66. A food product comprising a free flowing powder of claim 61.

67. Colorant for beverages comprising a free flowing powder of claim 61.

68. Colorant for cosmetics comprising a free flowing powder of claim 61.

69. Colorant for dietary supplements comprising a free flowing powder of claim 61.

70. Colorant for food products comprising a free flowing powder of claim 61.

* * * * *